US010786633B2

(12) United States Patent
Tsai et al.

(10) Patent No.: US 10,786,633 B2
(45) Date of Patent: Sep. 29, 2020

(54) NEBULIZER AND NOZZLE ASSEMBLY THEREOF

(71) Applicant: HCMed Innovations Co., LTD, Taipei (TW)

(72) Inventors: Wen-Yu Tsai, New Taipei (TW); Chieh-Sheng Cheng, Taipei (TW); Chien-Shen Tsai, New Taipei (TW)

(73) Assignee: HCMed Innovations Co., LTD., Taipei (TW)

(*) Notice: Subject to any disclaimer, the term of this patent is extended or adjusted under 35 U.S.C. 154(b) by 405 days.

(21) Appl. No.: 15/699,547

(22) Filed: Sep. 8, 2017

(65) Prior Publication Data

US 2019/0076605 A1 Mar. 14, 2019

(51) Int. Cl.
*A61M 11/00* (2006.01)
*A61M 15/00* (2006.01)
(Continued)

(52) U.S. Cl.
CPC ........ *A61M 11/00* (2013.01); *A61M 15/0021* (2014.02); *A61M 16/0858* (2014.02);
(Continued)

(58) Field of Classification Search
CPC .... A61M 11/00; A61M 11/08; A61M 15/002; A61M 15/0021; A61M 15/0095; A61M 2016/0018; A61M 2016/0021; A61M 2016/0027; A61M 16/021; A61M 16/022; A61M 2205/3331; A61M 2206/11;
(Continued)

(56) References Cited

U.S. PATENT DOCUMENTS 9,302,060 B2 * 4/2016 Denyer ................ A61M 15/00
9,956,360 B2 * 5/2018 Germinario ......... A61M 16/021
(Continued)

FOREIGN PATENT DOCUMENTS

EP 2 119 465 11/2009

OTHER PUBLICATIONS

International Search Report and Written Opinion of The International Searching Authority dated Nov. 9, 2018, issued in International Application No. PCT/US2018/050033.

*Primary Examiner* — Rachel T Sippel
*Assistant Examiner* — Benjamin M. Kusiak
(74) *Attorney, Agent, or Firm* — Perkins Coie LLP

(57) ABSTRACT

A nebulizer utilizing a nozzle assembly includes a main conduit and an air pressure duct. The main conduit is disposed on the nebulizer and has an inner surface and an outer surface. The main conduit has an atomizing opening. The air pressure duct is disposed on one of the inner surface and the outer surface of the main conduit, and has a connecting opening connected to the sensor and a detecting opening that is exposed and adjacent to the atomizing opening. The sensor is disposed inside the nebulizer and determines a pressure change of the atomizing opening by detecting the pressure of the detecting opening. The nebulizer includes an atomizing module and a controlling module electrically connected to the atomizing module and the sensor, and the controlling module determines whether the atomizing module should be turned on based on the pressure change of the atomizing opening detected by the sensor.

22 Claims, 9 Drawing Sheets

(51) Int. Cl.
*A61M 16/08* (2006.01)
*A61M 16/00* (2006.01)

(52) U.S. Cl.
CPC ............... *A61M 2016/0021* (2013.01); *A61M 2205/3331* (2013.01); *A61M 2209/10* (2013.01)

(58) Field of Classification Search
CPC .......... A61M 2209/10; A61M 15/0086; A61M 15/0088; A61M 15/0091–0098; A61M 16/0841; A61M 16/0858
USPC ........................................ 128/200.14–200.23
See application file for complete search history.

(56) References Cited

U.S. PATENT DOCUMENTS

| | | | | |
|---|---|---|---|---|
| 2010/0092397 | A1* | 4/2010 | Hofmann | A61K 9/0078<br>424/43 |
| 2011/0108025 | A1* | 5/2011 | Fink | A61M 11/005<br>128/200.16 |
| 2011/0240015 | A1* | 10/2011 | Nikander | A61M 15/00<br>128/200.14 |
| 2011/0290241 | A1 | 12/2011 | Maeda et al. | |
| 2014/0116426 | A1 | 5/2014 | Mullinger et al. | |
| 2014/0251321 | A1* | 9/2014 | Benson | A61M 15/009<br>128/200.23 |
| 2014/0299125 | A1 | 10/2014 | Buchberger | |
| 2017/0106155 | A1* | 4/2017 | Reed | A61M 11/00 |
| 2017/0304561 | A1* | 10/2017 | Hazani | A61M 15/00 |
| 2019/0290879 | A1* | 9/2019 | Kern | A61M 16/024 |

* cited by examiner

NEBULIZER AND NOZZLE ASSEMBLY THEREOF

BACKGROUND

1. Technical Field

The present disclosure relates to medical devices, and in particular, to a nebulizer and a nozzle assembly thereof.

2. Description of Related Art

Medical nebulizers are mainly employed in administering medication to patients through patients' respiratory systems. The nebulizer atomizes liquid medication as tiny liquid droplets each having a certain particle size, so that a patient can inhale the atomized medication into the respiratory system through respirations. By means of the nasal and oral administration, the drugs can be successfully administered into the patient's circulatory system to accomplish the treatment.

The conventional nebulizer is designed to continuously atomize medication as atomized liquids each having the identical atomization quantity without taking a patient's respiratory rate and vital capacity into account when the nebulizer starts to work. However, such a manner may affect the amount of medication the patient inhales. In addition, when patients are treated by aerosol inhalation, the continuously sprayed atomized liquids each having the identical atomization quantity would lead to low bioavailability of drugs and inconvenience to patients due to patients' respective respiratory rates.

BRIEF DESCRIPTION OF THE DRAWINGS

The accompanying drawings are included to provide a further understanding of the present disclosure, and are incorporated in and constitute a part of this specification. The drawings illustrate example embodiments of the present disclosure and, together with the description, serve to explain the principles of the present disclosure.

DETAILED DESCRIPTION

Figure 1:
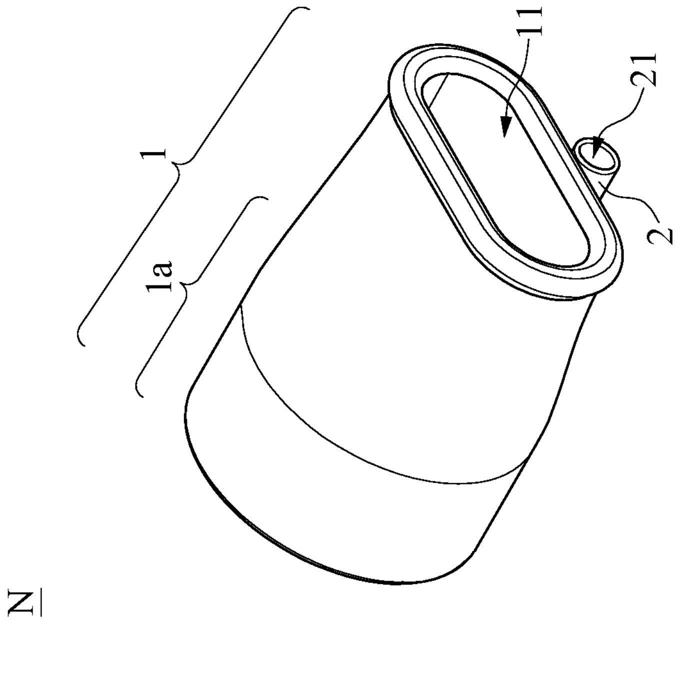
FIG. 1 is a schematic view of a nozzle assembly in which an air pressure duct is disposed on an outer surface of the main conduit according to some embodiments of the present disclosure.

As discussed above, the conventional medicinal nebulizers have the drawback of low bioavailability of drugs, and lack the capability to adapt to each individual patient's different respiratory rate. Accordingly, introduced herein is a nebulizer and a nozzle assembly that can detect the air pressure changes of the main conduit opening and, in response to the detected pressure changes, automatically control the nebulizer to turn on or to turn off, so as to achieve better atomization efficiency.

It is further observed here that, for the detection of the air pressure changes of the main conduit of the nozzle assembly, a straightforward solution would be to place the sensor at the main conduit and close to the user piece (e.g., a mouth piece or a mask) where the user inhales. However, in practice, such sensor location makes the sensor susceptible to water or other moisture damage, thereby causing a reliability issue. Embedding the sensor in a waterproof way in the nozzle assembly would most likely increase the cost of the nozzle assembly to an undesirable degree, making the overall unit too expensive for consumers to purchase and/or maintain. Moreover, in practice, the machine would be regularly cleaned by the user (e.g., with water or other cleaner, such as a water-soap mix). It is desirable to have an automatic nebulizer that is affordable, reliable, durable, and easy to clean.

Accordingly, disclosed here is a nebulizer device that utilizes a nozzle assembly which includes a main conduit and an air pressure duct. The main conduit can be attached to the nebulizer and has an inner surface and an outer surface. The main conduit has an atomizing opening and guides the atomized fluid to the user (through a user piece, e.g., a mouth piece or a mask). In some embodiments, the air pressure duct can be disposed on the inner surface or the outer surface of the main conduit, and the duct has a connecting opening connected to the sensor and a detecting opening that is exposed and adjacent to the atomizing opening. Accordingly to the present disclosure, the sensor can be disposed inside the nebulizer, and the sensor determines a pressure change of the atomizing opening by detecting the pressure of the detecting opening. Furthermore, the nebulizer includes an atomizing module and a controlling module electrically connected to the atomizing module and the sensor, and the controlling module determines whether the atomizing module should be turned on, according to pressure change of the atomizing opening detected by the sensor.

According to another aspect of the present disclosure, a nozzle assembly disclosed here includes a main conduit and an air pressure duct. The main conduit has an inner surface and an outer surface, and the main conduit has an atomizing opening. The air pressure duct can be on the inner surface and the outer surface of the main conduit. Furthermore, the air pressure duct has a connecting opening connected to a sensor and a detecting opening that is exposed and adjacent to the atomizing opening, and the sensor determines the pressure change of atomizing opening by detecting the pressure of the detecting opening.

With the disclosed embodiments herein, the nebulizer and the nozzle assembly thereof resolve the aforementioned drawbacks of conventional nebulizers. Various embodiments of the present disclosure are described in more detail below with regard to the figures. In order to further understand the techniques, means and effects of the present disclosure, the following detailed descriptions and appended drawings are hereby referred to, such that, and through which, the purposes, features and aspects of the present disclosure can be thoroughly and concretely appreciated; however, the appended drawings are merely provided for reference and illustration, without any intention to be used for limiting the present disclosure.

In the following, numerous specific details are set forth to provide a thorough understanding of the presently disclosed technology. In other embodiments, the techniques introduced here can be practiced without these specific details. In other instances, well-known features, such as specific fabrication techniques, are not described in detail in order to avoid unnecessarily obscuring the present disclosure. References in this description to "an embodiment," "one embodiment," or the like, mean that a particular feature, structure, material, or characteristic being described is included in at least one embodiment of the present disclosure. Thus, the appearances of such phrases in this specification do not necessarily all refer to the same embodiment. On the other hand, such references are not necessarily mutually exclusive either. Furthermore, the particular features, structures, materials, or characteristics can be combined in any suitable manner in one or more embodiments. Also, it is to be understood that the various embodiments shown in the figures are merely illustrative representations and are not necessarily drawn to scale.

The terms "coupled" and "connected," along with their derivatives, can be used herein to describe structural relationships between components. It should be understood that these terms are not intended as synonyms for each other. Rather, in particular embodiments, "connected" can be used to indicate that two or more elements are in direct contact with each other. Unless otherwise made apparent in the context, the term "coupled" can be used to indicate that two or more elements are in either direct or indirect (with other intervening elements between them) contact with each other, or that the two or more elements co-operate or interact with each other (e.g., as in a cause and effect relationship), or both.

Some embodiments of the present disclosure described below can take the form of computer- or controller-executable instructions, including routines executed by a programmable computer or controller. Those skilled in the relevant art will appreciate that the introduced techniques can be practiced on computer or controller systems other than those shown and described below. The techniques introduced herein can be embodied in a special-purpose computer or data processor that is specifically programmed, configured or constructed to perform one or more of the computer-executable instructions described below. Accordingly, the terms "computer" and "controller" as generally used herein refer to any data processor and can include Internet-capable appliances and handheld devices (including palm-top computers, wearable computers, cellular or mobile phones, multi-processor systems, processor-based or programmable consumer electronics, network computers, mini computers and the like). Information handled by these computers and controllers can be presented at any suitable display medium, including a liquid crystal display (LCD) or a light-emitting diode (LED) display. Instructions for performing computer- or controller-executable tasks can be stored in or on any suitable computer-readable medium, including hardware, firmware or a combination of hardware and firmware.

Figure 2:
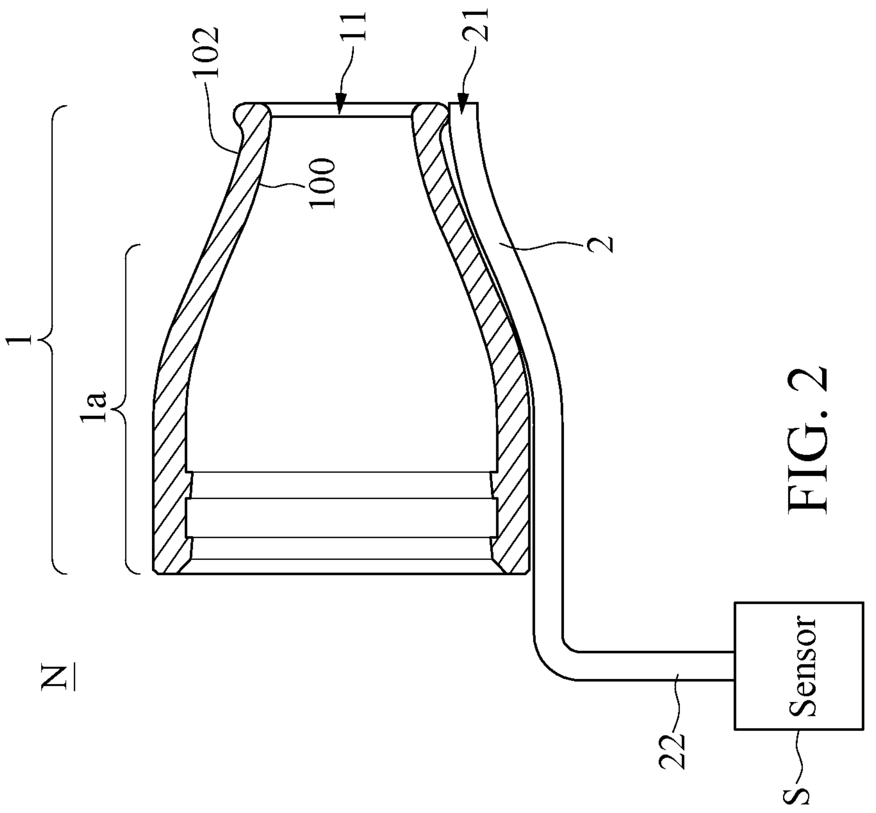
FIG. 2 is a sectional view of the nozzle assembly in which the air pressure duct is disposed on the outer surface of the main conduit according to some embodiments of the present disclosure.

FIG. 1 is a schematic view of a nozzle assembly in which an air pressure duct is disposed on an outer surface of the main conduit according to the present disclosure, and FIG. 2 is a sectional view of the nozzle assembly in which the air pressure duct is disposed on the outer surface of the main conduit according to the present disclosure.

As shown in FIGS. 1-2, a nozzle assembly N and a nebulizer D including the nozzle assembly N according to the present disclosure include a main conduit 1 and an air pressure duct 2. The main conduit 1 has an inner surface 100, an outer surface 102 and an atomizing opening 11. The air pressure duct 2 is disposed on one of the inner surface 100 and the outer surface 102 of the main conduit 1. In addition, the air pressure duct 2 has a connecting opening 22 and a detecting opening 21. The connecting opening 22 is connected to a sensor S, and the detecting opening 21 is exposed and adjacent to the atomizing opening 11 of the main conduit 1. The sensor S determines a pressure change of the atomizing opening 11 via the pressure of the detecting opening 21.

The present disclosure provides a nozzle assembly N, which includes a main conduit 1 and an air pressure duct 2, as shown in FIGS. 1 and 2. The main conduit 1 has an inner surface 100 and an outer surface 102. According to the appearance, the main conduit 1 of the present disclosure can have a conical portion 1*a*, showing a conical shape that tapers smoothly from the body to the opening, and the atomizing opening 11 is disposed on the narrow position of the conical portion 1*a*, but not limited thereto. The atomizing opening 11 is used for delivering droplets, mists, liquids, gases or the combination thereof.

The air pressure duct 2 is disposed on the outer surface 102 of the main conduit 1, and preferably, the air pressure duct 2 is disposed on and tightly attached to the outer surface 102 of the main conduit 1, but it can be modified according to practical needs. The air pressure duct 2 has two openings respectively at each end thereof, in which one end is the connecting opening 22 and the other end is the detecting opening 21. More specifically, the connecting opening 22 and the detecting opening 21 can be respectively disposed at each end of the air pressure duct 2, and the air pressure duct 2 can be formed as a conduit, but is not limited thereto. In other words, the air pressure duct 2 of the present disclosure can be a single-piece or a multi-piece. In the present embodiment, the air pressure duct 2 is a single-piece for an exemplification. It should be noted that the internal space of the air pressure duct 2 and that of the main conduit 1 are separated and isolated from each other. The detecting opening 21 of the air pressure duct 2 is exposed and adjacent to the atomizing opening 11 of the main conduit 1. The detecting opening 21 of the air pressure duct 2 is aligned with the atomizing opening 11 of the main conduit 1.

On the other hand, the connecting opening 22 of the air pressure duct 2 is connected to the sensor S that is disposed outside the nozzle assembly N. Therefore, the sensor S detects the pressure change via the detecting opening 21.

More specifically, when a user closes his/her lips around the nozzle assembly N, the atmosphere around the detecting opening 21 will generate pressure changes. The air can flow through the air pressure duct 2 to the sensor S connected with the connecting opening 22, such that the sensor S can detect the change of air pressures via the air pressure duct 2.

It should be noted that the atomizing opening 11 and the detecting opening 21 have the same atmosphere since the detecting opening 21 of the air pressure duct 2 is adjacent to the atomizing opening 11 of the main conduit 1, such that the pressure change of the detecting opening 21 detected by the sensor S is equal to that of the atomizing opening 11. When the user closes his/her lips around the nozzle assembly N, the lips enclose both the atomizing opening 11 and the detecting opening 21. When the user inhales, a negative pressure is generated in the detecting opening 21 and the atomizing opening 11. Since a change of the air pressure in the atomizing opening 11 is equal to that of the air pressure in the detecting opening 21, the pressure change of the detecting opening 21 detected by the sensor S can be regarded as a pressure change of the atomizing opening 11 of the nozzle assembly N.

Figure 4:
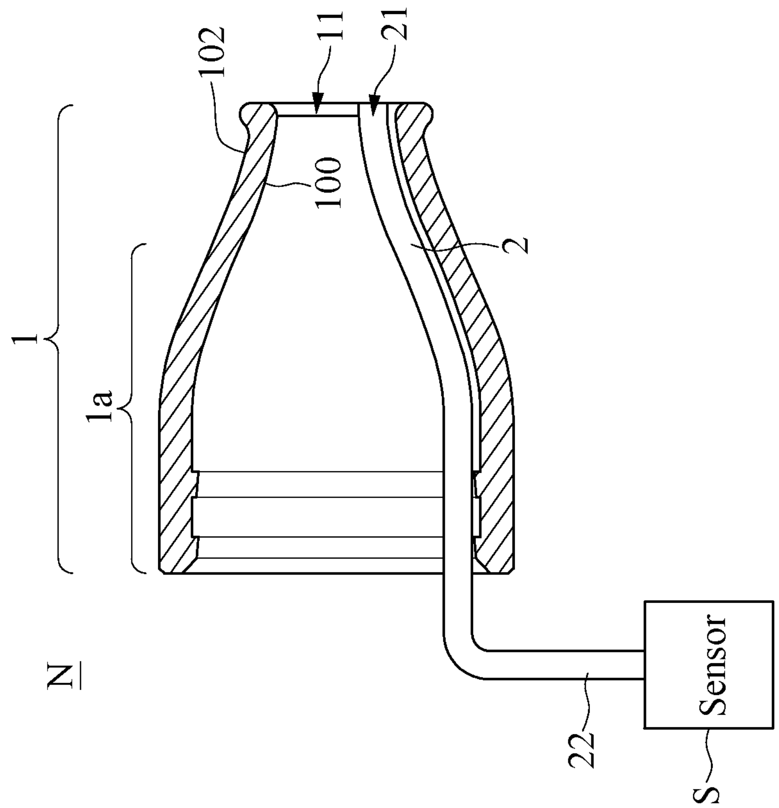
FIG. 4 is a sectional view of the nozzle assembly in which the air pressure duct is disposed on the inner surface of the main conduit according to some embodiments of the present disclosure.
Figure 3:
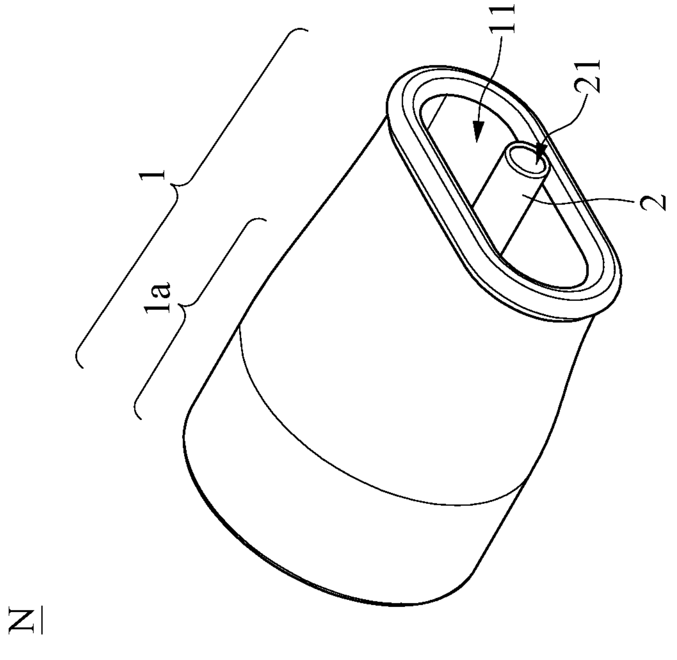
FIG. 3 is a schematic view of the nozzle assembly in which the air pressure duct is disposed on an inner surface of the main conduit according to some embodiments of the present disclosure.

FIG. 3 and FIG. 4 show the nozzle assembly N according to another embodiment of the present disclosure. The difference between the nozzle assembly N illustrated in FIGS. 3 & 4 and that illustrated in FIGS. 1 & 2 is that the air pressure duct 2 is disposed on the inner surface 100 of the main conduit 1. No matter where the air pressure duct 2 is disposed on the inner surface 100 or the outer surface 200 of the main conduit 1, the viscosity of the laminar flow will not be affected. In the nozzle assembly N of the present disclosure, the detecting opening 21 of the air pressure duct 2 is close to the atomizing opening 11, so the sensor S can detect the pressure change of the main conduit 1 via the detecting opening 21.

According to the present disclosure, a nebulizer D is provided. The nebulizer D includes a main assembly B, an accommodating assembly A and the nozzle assembly N of the present disclosure. The main assembly B includes a first casing 3, a controlling module C and a sensor S, in which the controlling module C and the sensor S are both disposed in the first casing 3. The accommodating assembly A is detachably disposed on the main assembly B, and the accommodating assembly A includes a second casing 4 and an atomizing module E. The nozzle assembly N is detachably disposed on the accommodating assembly A.

Figure 5:
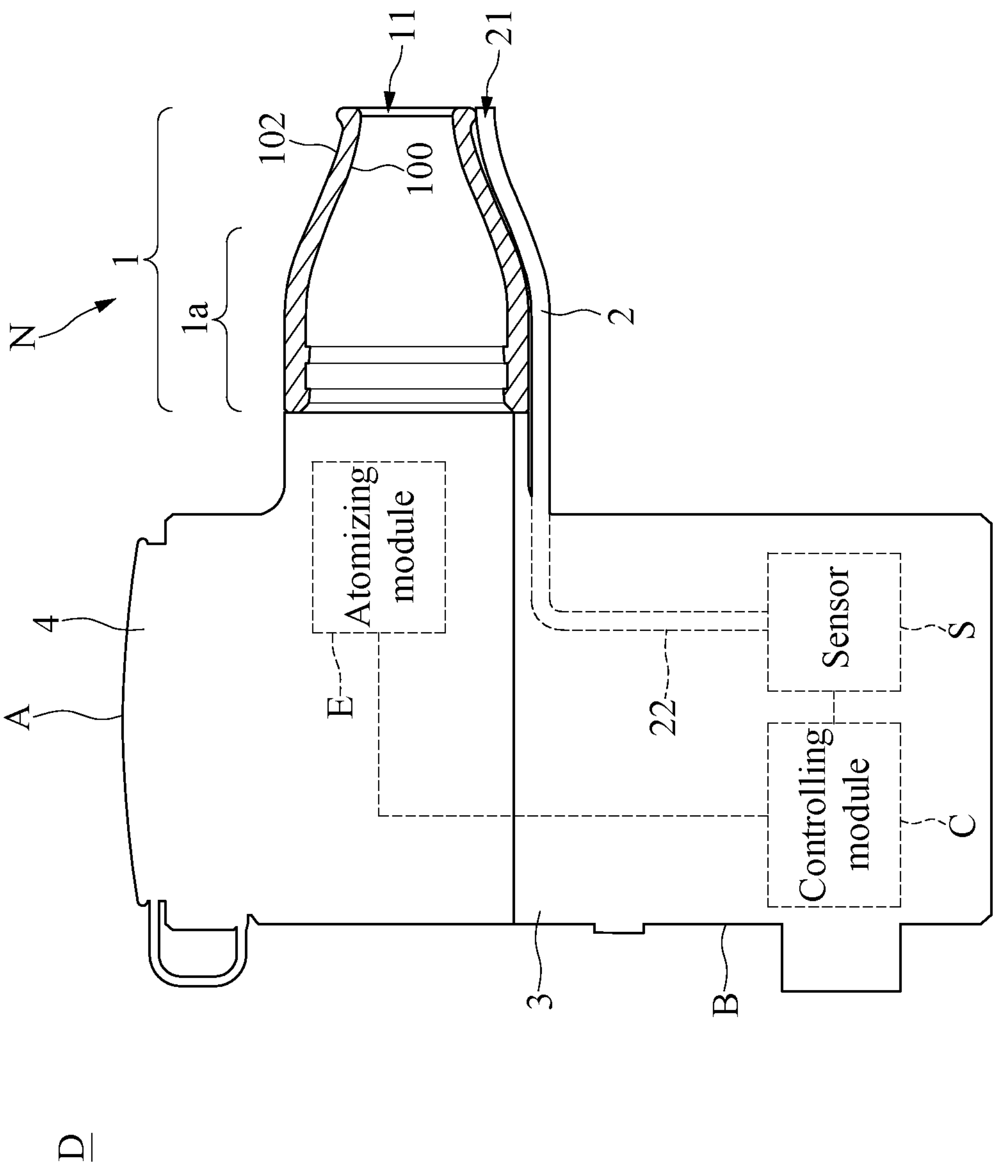
FIG. 5 is a functional view of the nozzle assembly of a nebulizer in which the air pressure duct is disposed on the outer surface of the main conduit according to some embodiments of the present disclosure.
Figure 6:
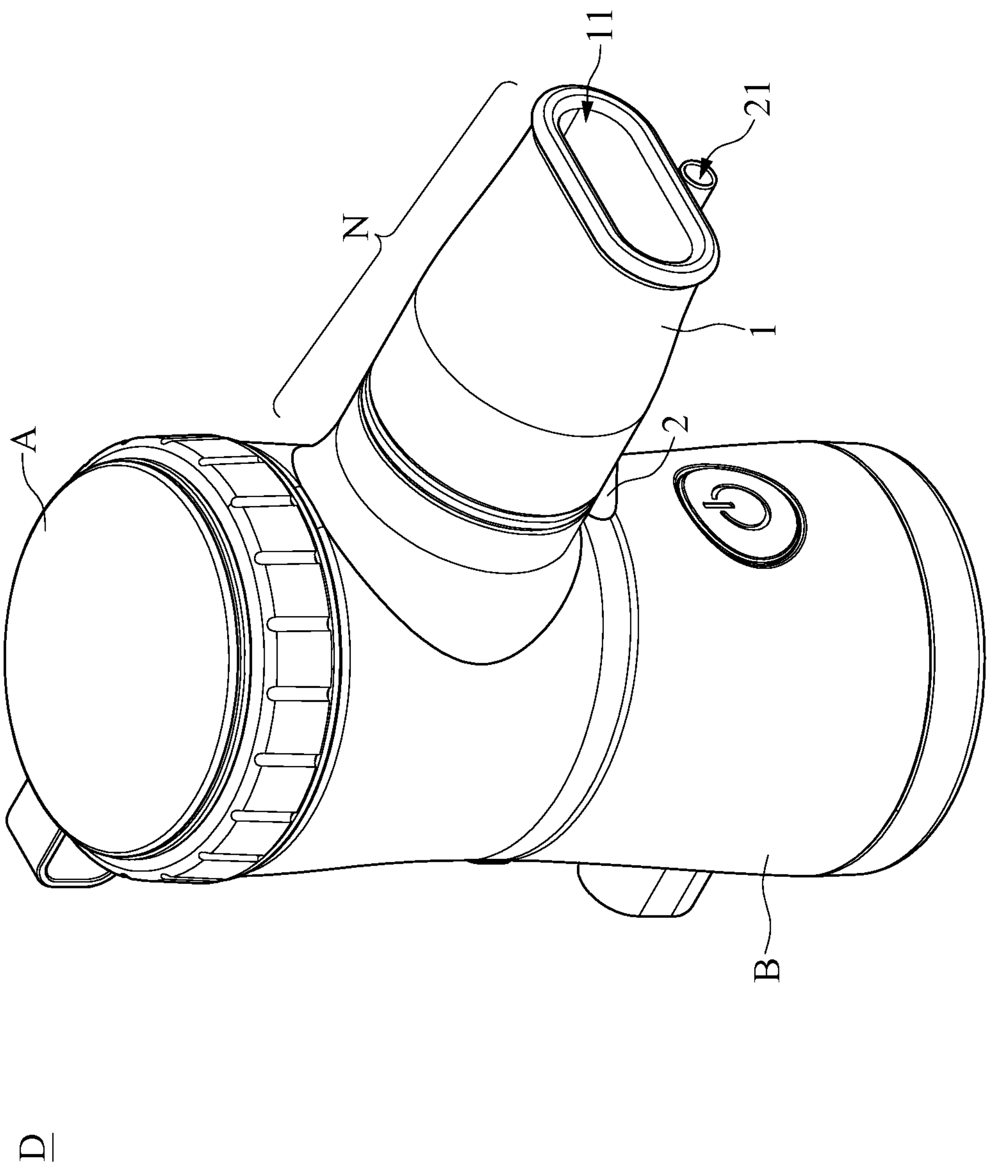
FIG. 6 is a schematic view of the nozzle assembly of the nebulizer in which the air pressure duct is disposed on the outer surface of the main conduit according to some embodiments of the present disclosure.
Figure 7:
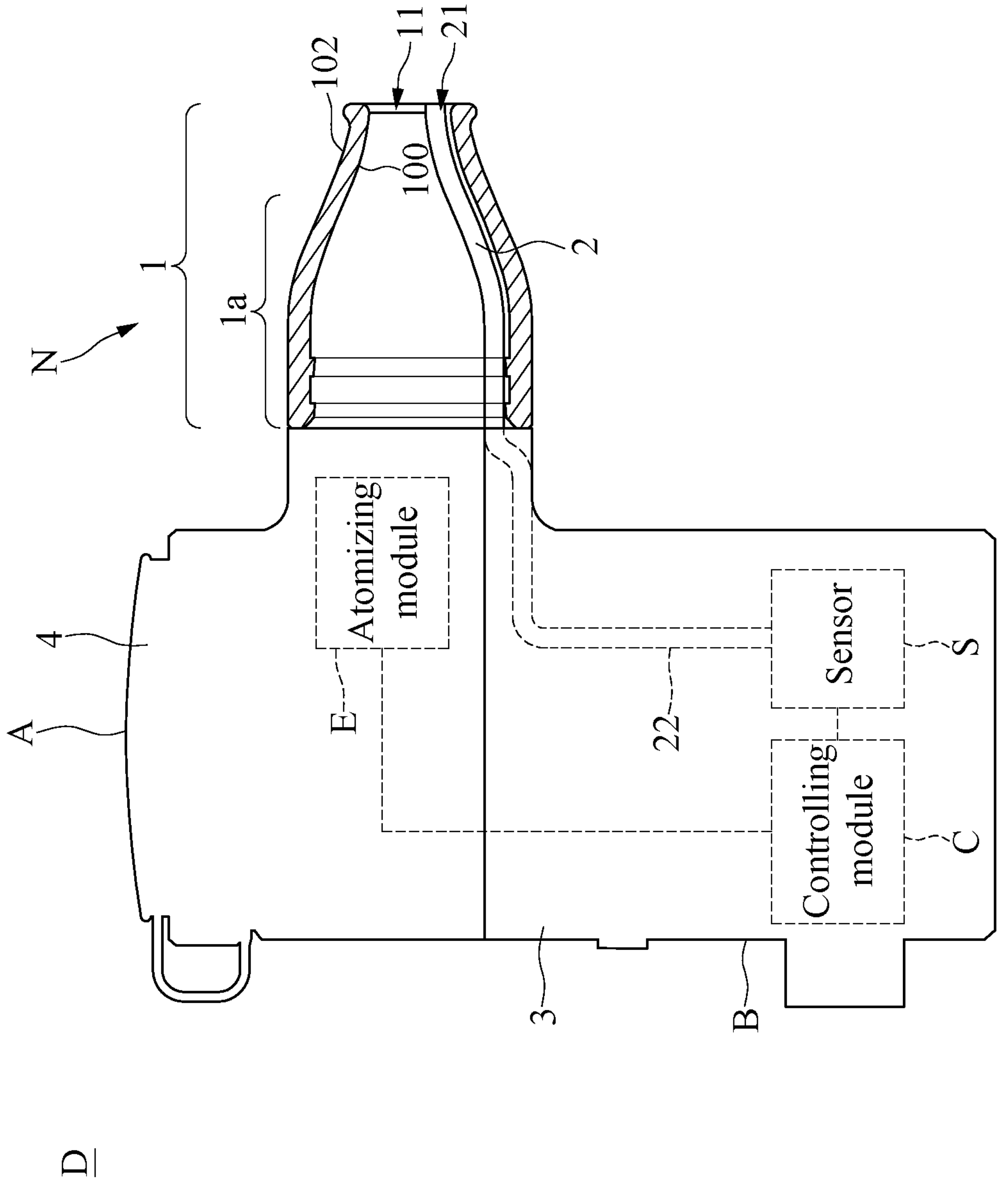
FIG. 7 is a functional view of the nozzle assembly of the nebulizer in which the air pressure duct is disposed on the inner surface of the main conduit according to some embodiments of the present disclosure.
Figure 8:
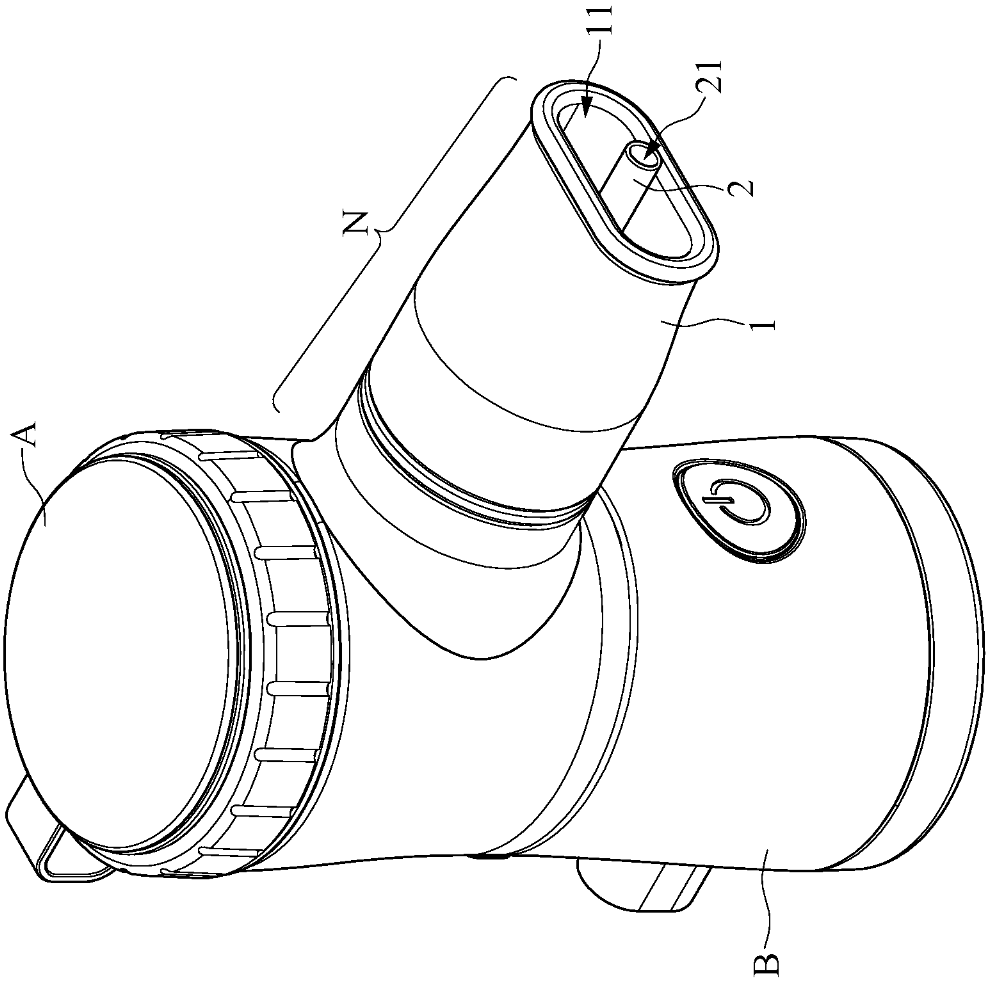
FIG. 8 is a schematic view of the nozzle assembly of the nebulizer in which the air pressure duct is disposed on the inner surface of the main conduit according to some embodiments of the present disclosure.

FIG. 5 to FIG. 8 show the nebulizer D including the nozzle assembly N according to the present disclosure. FIG. 5 and FIG. 6 illustrate that the air pressure duct 2 of the nozzle assembly N is disposed on the outer surface 102 of the main conduit 1, and FIG. 7 and FIG. 8 illustrate that the air pressure duct 2 of the nozzle assembly N is disposed on the inner surface 100 of the main conduit 1.

More specifically, the nebulizer D of the present disclosure utilizes the aforementioned nozzle assembly N, and the nebulizer D includes the main assembly B, the accommodating assembly A and the aforementioned nozzle assembly N.

The main assembly B includes the first casing 3, the controlling module C and the sensor S, in which the controlling module C and the sensor S are both disposed in the first casing 3. The controlling module C and the sensor S are electrically connected to each other.

The accommodating assembly A is detachably disposed on the main assembly B, and the accommodating assembly A and the main assembly B can be detachable from each other or can be assembled together. The accommodating assembly A includes the second casing 4 and the atomizing module E disposed therein. Similarly, the atomizing module E can be detachably disposed in the second casing 4 and electrically connected to the controlling module C.

The nozzle assembly N is detachably disposed on the accommodating assembly A, and the nozzle assembly N includes the main conduit 1 and the air pressure duct 2. The air pressure duct 2 can be disposed on the outer surface 102 or the inner surface 100 of the main conduit 1. The description of the main conduit 1 and the air pressure duct 2 has been illustrated above, and is omitted herein for the sake of brevity.

As stated above, the air pressure duct 2 of the nozzle assembly N of the nebulizer D has the connecting opening 22 and the detecting opening 21. Similarly, the connecting opening 22 of the air pressure duct 2 of the present disclosure is connected to the sensor S disposed in the main assembly B, and the detecting opening 21 is adjacent to the atomizing opening 11 of the main conduit 1. When the user closes his/her lips around the nozzle assembly N of the nebulizer D and the user inhales, a negative pressure will be generated around the atomizing opening 11 and the detecting opening 21. The sensor S disposed in the main assembly N can detect a change of the air pressure in the detecting opening 21 via the laminar flow in the air pressure duct 2. Since the change of the air pressure in the atomizing opening 11 is equal to that of the air pressure in the detecting opening 21, the pressure change of the detecting opening 21 detected by the sensor S can be regarded as a pressure change of the atomizing opening 11 of the nozzle assembly N.

It should be noted that the sensor S is disposed in the first casing 3 of the main assembly B and electrically connected to the controlling module C of the nebulizer D according to the present embodiment. Therefore, no matter if the air pressure duct 2 of the nozzle assembly N is disposed in the inner surface 100 or the outer surface 102 of the main conduit 1, the body of the air pressure duct 2 extends into the interior of the main assembly B. In other words, the air pressure duct 2 does not pass through the second casing 4 of the accommodating assembly A, but passes through the first casing 3 of the main assembly B, such that the connecting opening 22 can be connected to the sensor S in the main assembly B. The accommodating assembly A is used for accommodating medicines, and the atomizing module E in the accommodating assembly A can be detachable to allow users to clean it. Therefore, by virtue of the above configuration, the air pressure duct 2 of the nebulizer D of the present disclosure does not pass through the accommodating assembly A, thereby enhancing the easy-to-use nature.

As stated above, the nozzle assembly N of the nebulizer D of the present disclosure has the air pressure duct 2 of which the connecting opening 22 is connected to the sensor S in the main assembly B. The pressure change at the detecting opening 21 is detected by the sensor S via the air pressure duct 2 and converted into a sensing signal, and the sensing signal is subsequently transmitted to the controlling module C disposed in the main assembly B. Afterwards, the controlling module C sends a controlling signal, by which the atomizing module E of the accommodating assembly A is turned on to atomize. In practice, the nebulizer D is not turned on at the beginning. When a user closes his/her lips around the nozzle assembly N and the patient inhales, the air of the interior of the nozzle assembly N (including the atomizing opening 11 and the detecting opening 21) flows toward the mouth of the user, so as to produce a negative pressure with respect to the exterior of the nozzle assembly N. The sensor S detects the negative pressure to generate a negative pressure signal and transmits the negative pressure signal to the controlling module C. Then, the controlling module C produces a starting signal based on the negative pressure signal, and transmits the starting signal to the atomizing module E. After receiving the starting signal, the atomizing module E starts to atomize the liquid medicines in the accommodating assembly A. The atomized drugs can be actively administered into the user's body by the atomizing module E, or be passively administered into the user's body by inhalation.

On the other hand, when the user stops inhaling or the user's lips leave the nozzle assembly N, the sensor S stops to sense any pressure changes because the air therein stops flowing. Hence, the controlling module C does not receive any negative pressure signals and provides a stop signal to the atomizing module E, such that the atomizing module E stops atomizing after receiving the stop signal.

By the virtue of the above configuration, the nebulizer D of the present disclosure can provide a user with a controlled amount of atomized medicines based on the user's respiratory rate, so that when the user takes a breathe, the medication immediately stops being atomized. As a result, users or patients can be administered with an amount of medicines more precisely, and the bioavailability can be improved.

Figure 9:
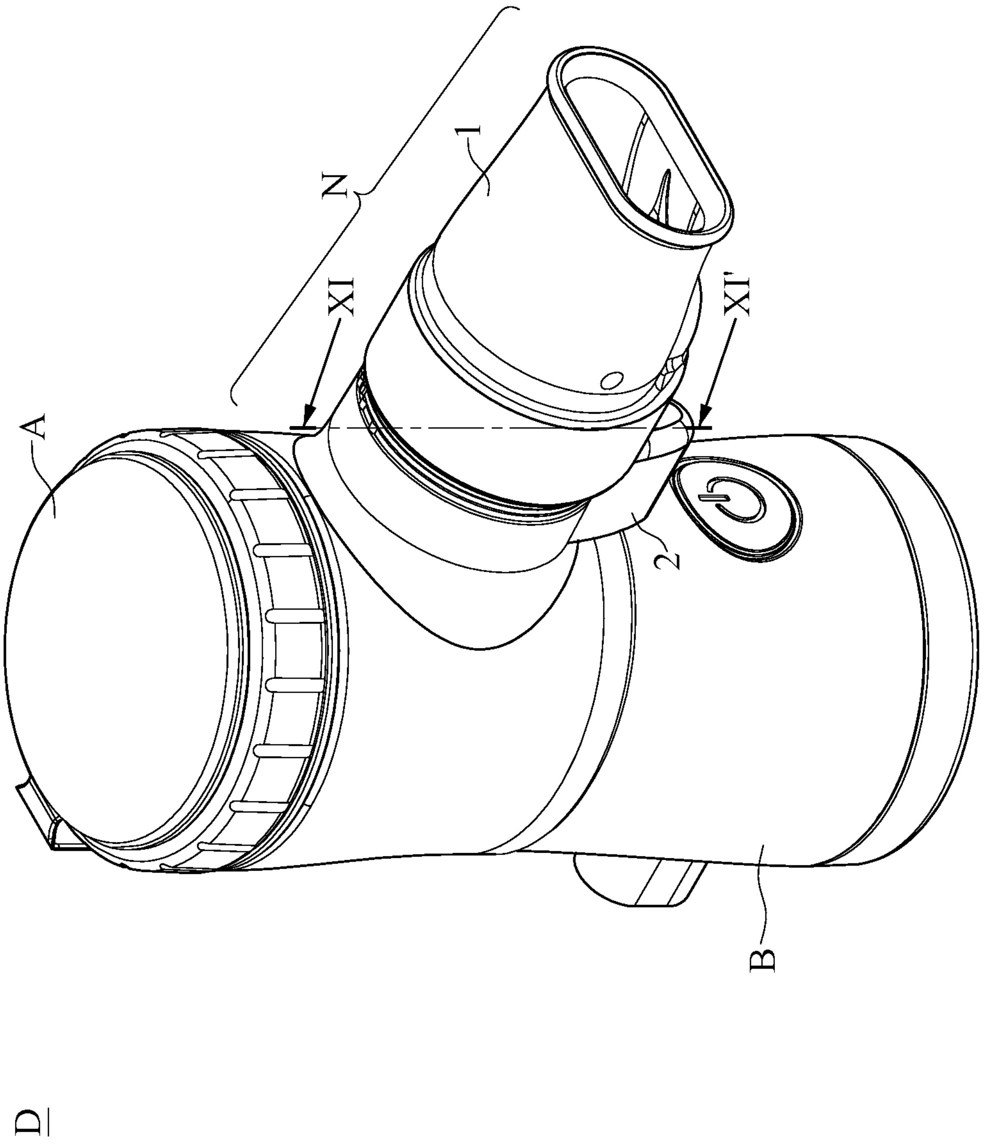
FIG. 9 is a schematic view of a nozzle assembly of a nebulizer according to an embodiment of the present disclosure.
Figure 10:
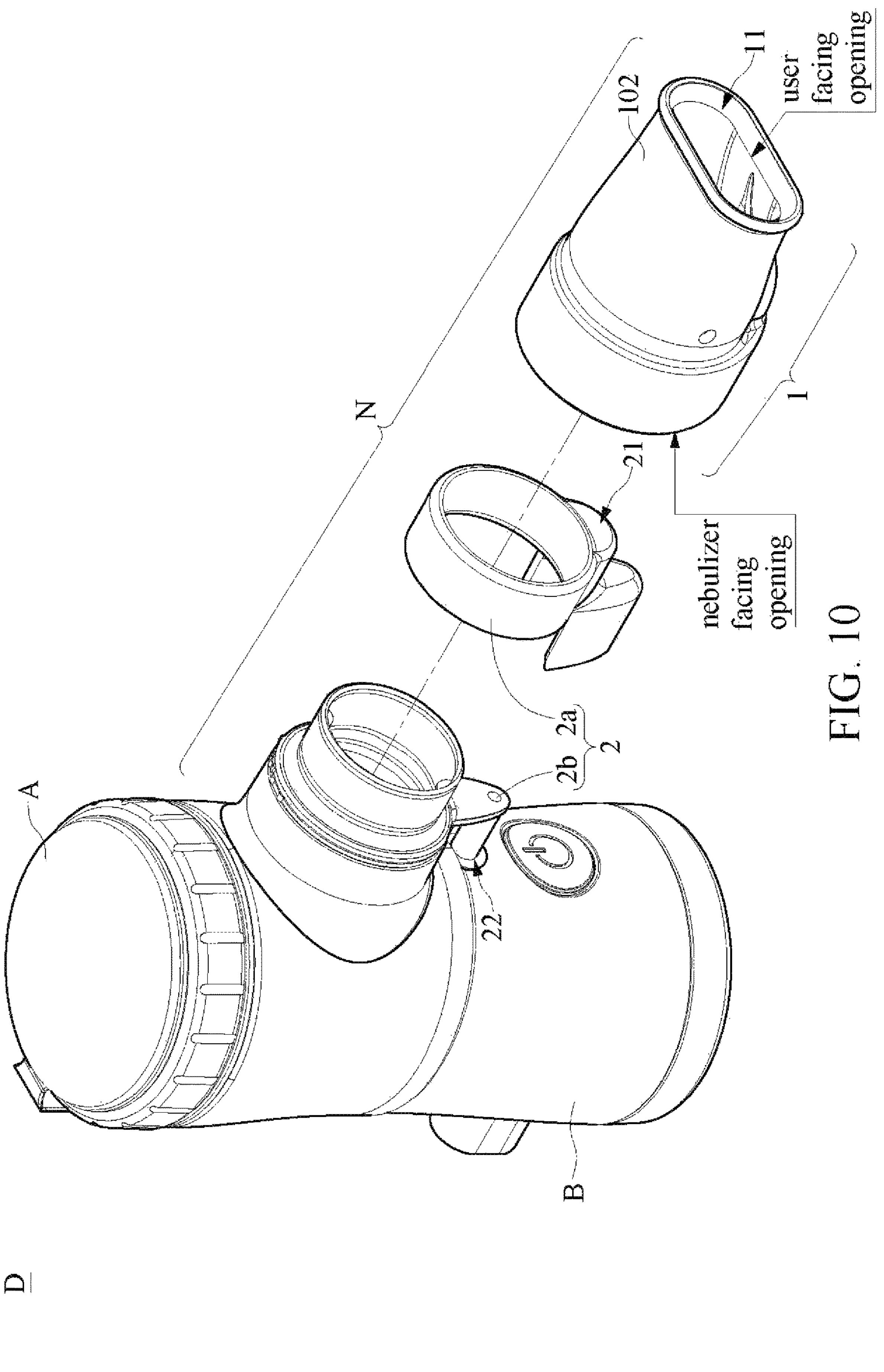
FIG. 10 is an exploded diagram of the nozzle assembly of the nebulizer according to the embodiment of FIG. 9.
Figure 11:
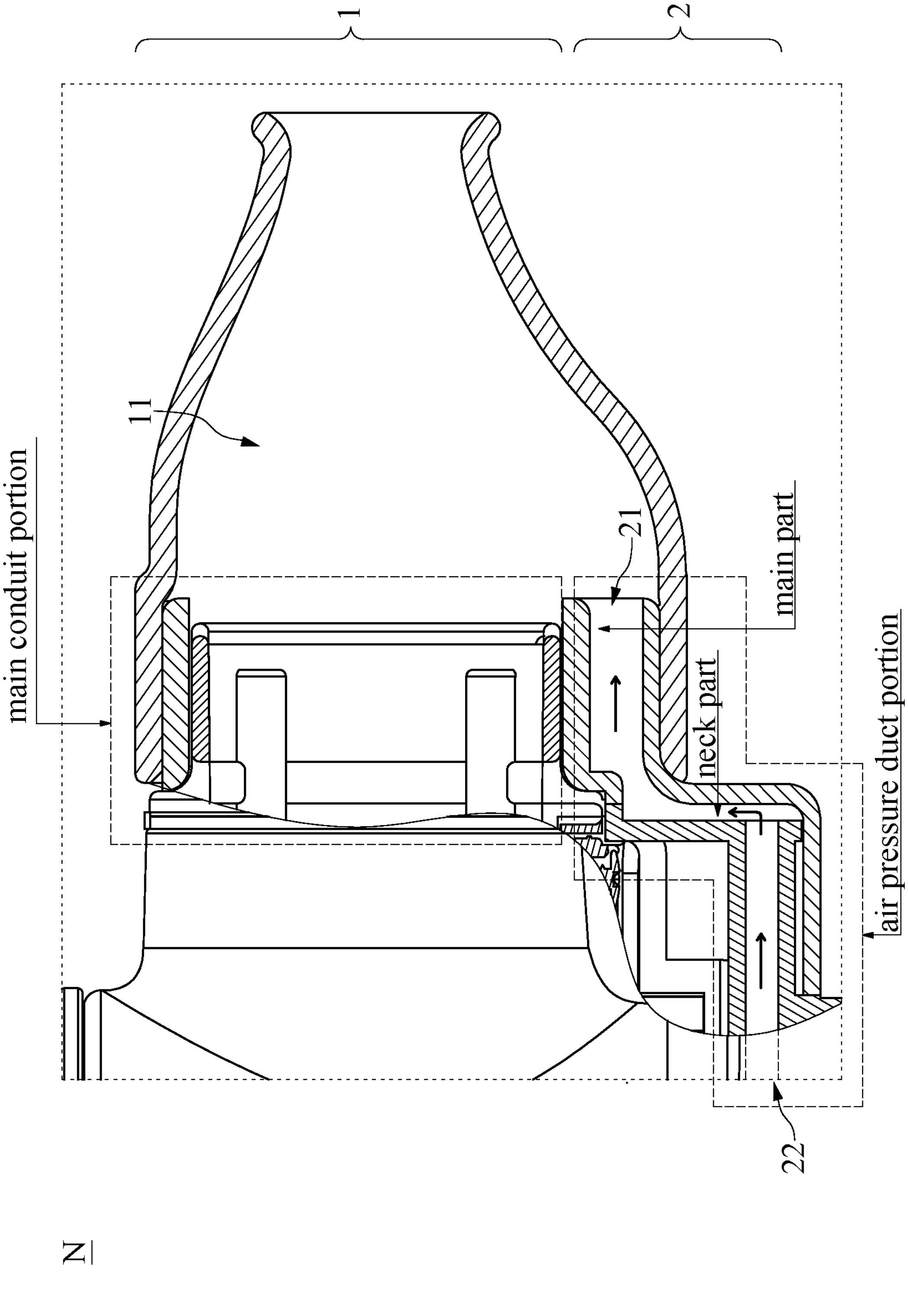
FIG. 11 is a sectional view of the nozzle assembly, including the main conduit and the air pressure conduit, as well as the user piece, according to the embodiment of FIG. 9 (along line XI-XI').

Referring to FIG. 9 to FIG. 11, FIG. 9 to FIG. 11 show a nebulizer D according to an embodiment of the present disclosure. The nozzle assembly N of the nebulizer D includes a main conduit 1 and an air pressure duct 2.

As mentioned above, the disclosed embodiments of the nebulizer strategically place the air sensor (e.g., used for detecting user inhalation) in the main body because of water proofing concerns. The embodiments utilize a nozzle assembly that can be detached for easier cleaning, and the air pressure duct portion in the nozzle assembly can enable the sensor in the main body to detect air pressure change (e.g., a negative air pressure).

Furthermore, it is observed here that the size and shape of the air pressure duct can affect the sensitivity of the air pressure sensor-generally speaking, the sensitivity is inversely proportional to the size of the air pressure duct. As such, in the embodiment shown in FIGS. 9-11, the air pressure duct portion is shaped to increase the lowest amount of air pressure change detectable by the sensor as compared to without the nozzle assembly. As shown in FIG. 11, the air pressure duct portion includes at least a neck part that has a cross sectional area smaller than a main part of the air pressure duct portion of the nozzle assembly N. In some embodiments, a cross sectional area of the main conduit portion is at least three (3) times larger than that of the main part of the air pressure duct portion. In addition, according to some implementations, a cross sectional area of the main part of the air pressure duct portion is at least thirty percent (30%) larger (or, 1.3 times larger) than that of the neck part of the air pressure duct portion. In one or more embodiments, the mechanical attachment of nozzle assembly N to the main body of the nebulizer D is substantially air tight (even though air tightness may not be necessary for a successful detection in embodiments disclosed herein).

On the other hand, it is observed that, with the nebulizer being regularly used, the nozzle assembly should be detachable and easily cleaned. If the air pressure duct is too narrow, water or other fluids may accumulate inside and may allow mold or bacteria to grow. Therefore, in one or more embodiments, the cross sectional area of the neck part is larger than a minimum value that allows a predetermined liquid (e.g., water or another cleansing liquid designated for cleaning the nozzle assembly) to evaporate within specification if the predetermined liquid enters the neck part. The exact specification depends on the actual application and the deployed environment. For example, for a specific application environment (e.g., senior living), a specification may provide that water in the neck shall be able to completely evaporate in a natural manner within one (1) hour under normal temperature and pressure (i.e., 20 degrees Celsius, 1 atm). Other application may require a different specification. According to certain embodiments, a cross sectional area of the main part of the air pressure duct portion is within a range of 15 $mm^2$ to 96 $mm^2$.

As shown in FIGS. 9-11, the nozzle assembly N can further include a user piece (e.g., a mouth piece as shown in FIG. 10 incorporating the main conduit 1, or a mask (not shown)). Depending on the implementation, the user piece can be mechanically attachable to the nozzle assembly N, or can be integrally formed as a portion of the nozzle assembly N. The mouth piece has a user facing opening suitable for user inhalation, and a nebulizer facing opening that is configured to cover both the main conduit portion and the air pressure duct portion of the nozzle assembly N.

FIG. 10 is an exploded perspective view showing the main conduit 1 and the air pressure duct 2, and the air pressure duct 2 of the present disclosure is disposed on the outer surface 102 of the main conduit 1 as a multi-piece. More specifically, the air pressure duct 2 is composed of a ring 2*a* and a duct 2*b*. The ring 2*a* is disposed along the outer surface 102 of the main conduit 1 to be a circular shape. The duct 2*b* is formed as a conducting which one end is connected to the ring 2*a* and the other end penetrates the main assembly B. Referring to FIG. 10 and FIG. 11, FIG. 11 is a sectional view along line XI-XI' in FIG. 9. The air pressure duct 2 has the detecting opening 21 adjacent to the atomizing opening 11 and the connecting opening 22 extending to connect the sensor (not shown), and the spaces between the detecting opening 21 and the connecting opening 22 are connected. When the user inhales, the air in the air pressure duct 2 flows, such that the air pressure around the detecting opening 21 changes, and the sensor detects the pressure change to transmit the sensing signal to the controlling module (not shown) in the main assembly B, thereby controlling the nebulizer to turn on. Similarly, the air pressure duct 2 does not pass through the accommodating assembly A, so as to enhance the convenience in use.

In other words, the controller can be configured to automatically activate the atomizer to dispense the fluid in response to the controller sensing a large enough air pressure change from the sensor, and can be further configured to automatically deactivate the atomizer to stop the dispensing of the fluid in response to the controller no longer sensing the large enough air pressure change. The large enough air pressure change may be a negative air pressure resulted from a user inhaling through the user piece. In some embodiments, the controller adjusts the control input (e.g., by turning on/off) when an absolute value of the air pressure change exceeds a threshold value. In addition or as an alternative to toggling on/off the atomizer, some embodiments of the controller can adjust the amount/speed/etc. that the atomizer atomizes and dispenses the therapeutic fluid (e.g., based on the air pressure change detected). In one or more embodiments, the air pressure change is a negative value, but alternatively the triggering air pressure change can be a positive value (e.g., when the user exhales). Note, however, that in the implementations where the controller may be triggered when the user exhales, adjustment needs to be made (e.g., the dispensing timing or the dispensing mechanism) to ensure that dispense of the atomized fluid does not cause user discomfort. In some implementation, the threshold value is 35 millibar (mbar).

Because the difference in application environment, in a number of embodiments, when the nebulizer is turned on, the nebulizer system can automatically calibrate the sensor to a neutral, zero state (e.g., which is equal to the atmospheric pressure at the moment and the location).

Additionally, because the different environment (e.g., different elevation) as well as the difference in each individual user (e.g., a child versus an elderly), it may be desirable for the air pressure triggering threshold to be adjustable. In one or more embodiments, the controller C is further configured to be able to enter a configuration mode (e.g., through the user activating a button on the nebulizer's main body, not shown for simplicity) and during the configuration mode, to receive an adjustment to the threshold value that triggers the automatic atomizing and dispensing of the therapeutic fluid in the nebulizer. According to some implementations, the adjustable range may be 10 mbar to 50 mbar. It is noted here that, for a female adult, it is typical for the triggering value to be around 35 mbar, for infant, 10 mbar, and for elderly, 20 mbar.

In addition or as an alternative to sensing an air pressure change (described above), some implementations of the controller may determine how to control the atomizer based on an absolute air pressure reading.

In the manners introduced above, the disclosed nebulizer and nozzle assembly thereof tackles the conventional nebulizers' drawback of low bioavailability of drugs, and lack the capability to adapt to each individual patient's different respiratory rate.

The descriptions illustrated herein set forth simply some example embodiments of the present disclosure; however, the characteristics of the present disclosure are by no means restricted thereto. All changes, alterations, or modifications conveniently considered by those skilled in the art are deemed to be encompassed within the scope of the present invention delineated by the following claims.

What is claimed is:

1. A nebulizer apparatus, comprising:
a main body that includes:
an atomizer operable to atomize a fluid stored in the main body in response to a control input,
a sensor configured to read an air pressure of a sensor opening disposed on a casing of the main body, and
a controller configured to receive the air pressure and, based at least in part on an air pressure change, adjust the control input of the atomizer; and
a nozzle assembly that is at least partially mechanically attachable to the main body, the nozzle assembly including:
a main conduit portion configured to guide the atomized fluid to a user piece, and
an air pressure duct portion that fluidly connects the sensor opening on the casing of the main body to the user piece via an air pressure detecting aperture, wherein the air pressure duct includes a duct and a separate ring, wherein the ring is removable from the main body, and wherein the ring includes the air pressure detecting aperture when detached from both the user piece and the main body.

2. The apparatus of claim 1, wherein the air pressure duct portion is shaped to increase an amount of air pressure change detectable by the sensor as compared to without the nozzle assembly.

3. The apparatus of claim 2, wherein the air pressure duct portion includes at least a neck part that has a cross sectional area smaller than a cross sectional area of a main part of the air pressure duct of the nozzle assembly.

4. The apparatus of claim 3, wherein the cross sectional area of the neck part is larger than a value that allows a predetermined liquid to evaporate within specification if the predetermined liquid enters the neck part.

5. The apparatus of claim 4, wherein the predetermined liquid is water or another cleansing liquid designated for cleaning the nozzle assembly.

6. The apparatus of claim 3, wherein a cross sectional area of the main part of the air pressure duct portion is within a range is within a range of 15 $mm^2$ to 96 $mm^2$.

7. The apparatus of claim 3, wherein a cross sectional area of the main conduit portion is at least 3 times larger than a cross sectional area of the main part of the air pressure duct portion.

8. The apparatus of claim 3, wherein a cross sectional area of the main part of the air pressure duct portion is at least 1.3 times larger than a cross sectional area of the neck part of the air pressure duct portion.

9. The apparatus of claim 1, wherein the controller adjusts the control input when an absolute value of the air pressure change exceeds a threshold value.

10. The apparatus of claim 9, wherein the air pressure change is a negative value.

11. The apparatus of claim 9, wherein the threshold value is 10 mbar to 50 mbar.

12. The apparatus of claim 9, wherein the controller is further configured to: during a configuration mode, receive an adjustment to the threshold value.

13. The apparatus of claim 1, wherein the controller is configured to automatically activate the atomizer to dispense the fluid in response to the controller sensing an amount of air pressure change from the sensor.

14. The apparatus of claim 13, wherein the controller is further configured to automatically deactivate the atomizer to stop the dispensing of the fluid in response to the controller no longer sensing the amount of air pressure change.

15. The apparatus of claim 14, wherein the air pressure change is negative.

16. The apparatus of claim 1, wherein the mechanical attachment of the nozzle assembly to the main body is substantially air tight.

17. The apparatus of claim 1, further comprising:
the user piece, wherein the user piece is mechanically attachable to the nozzle assembly.

18. The apparatus of claim 1, further comprising:
the user piece, wherein the user piece is integrally formed as a portion of the nozzle assembly.

19. The apparatus of claim 1, wherein the user piece has a user facing opening suitable for user inhalation, and a nebulizer facing opening that is configured to cover both the main conduit portion and the air pressure duct portion of the nozzle assembly.

20. The apparatus of claim 1, wherein the user piece is a mouth piece, and wherein the fluid is therapeutic.

21. The apparatus of claim 1, wherein the air pressure duct portion of the nozzle assembly is disposed on an outer side of the main conduit portion of the nozzle assembly.

22. A nebulizer apparatus, comprising:
a main body that includes:
an atomizer operable to atomize a fluid stored in the main body in response to a control input,
a sensor configured to read an air pressure of a sensor opening disposed on a casing of the main body, and a controller configured to receive the air pressure and, based at least in part on an air pressure change, adjust the control input of the atomizer; and a nozzle assembly that is at least partially mechanically attachable to the main body, the nozzle assembly including:

a main conduit portion configured to guide the atomized fluid through a user facing opening of a user piece, and an air pressure duct portion that fluidly connects the sensor opening on the casing of the main body to the user piece via a detecting opening, the detecting opening being arranged adjacent to the user piece, wherein the air pressure duct includes a duct and a separate ring, wherein the ring is removable from the main body, and wherein the ring includes the detecting opening when detached from both the user piece and the main body.

* * * * *